United States Patent [19]

Schwinn et al.

[11] 4,067,964
[45] Jan. 10, 1978

[54] ANTIHEMOPHILIC AGENT AND PROCESS FOR ITS MANUFACTURE

[75] Inventors: Horst Schwinn; Norbert Heimburger, both of Marburg an der Lahn, Germany

[73] Assignee: Behringwerke Aktiengesellschaft, Marburg an der Lahn, Germany

[21] Appl. No.: 739,278

[22] Filed: Nov. 5, 1976

[30] Foreign Application Priority Data

Nov. 7, 1975 Germany .............................. 2550011

[51] Int. Cl.² ............................................. A61K 35/50
[52] U.S. Cl. ..................................................... 424/105
[58] Field of Search ......................................... 424/105

[56] References Cited

U.S. PATENT DOCUMENTS

| 3,862,002 | 1/1975 | Sanders | 424/95 |
| 3,862,314 | 1/1975 | Zwisler et al. | 424/95 |

*Primary Examiner*—Sam Rosen
*Attorney, Agent, or Firm*—Curtis, Morris & Safford

[57] ABSTRACT

The invention relates to an antihemophilic agent, which may contain factor VIII, but also factor IV, VII and X activities and to a process for its manufacture by extracting placentae with an aqueous hypotonic medium, increasing the density of the extract and obtaining the supernatant layer forming thereupon.

16 Claims, No Drawings

ANTIHEMOPHILIC AGENT AND PROCESS FOR ITS MANUFACTURE

The present invention relates to an antihemophilic agent and to a process for its manufacture.

The antihemophilic agent having an extensive effect, which the invention relates to, mainly contains factor VIII and IX-activity, but also in a minor degree factor VII and X activities.

The invention also relates to a process for the manufacture of the antihemophilic agent and to preparations, especially to hemostyptics and coagulation active diagnostics, containing the antihemophilic agent as the essential active substance.

Blood coagulation is a complex process comprising several phases, based on various physiological and pathological reasons, its course depending on approximately 30 promoting and inhibiting factors. The decrease or increase of some of these blood coagulation factors may cause disturbances of the blood coagulation, sometimes manifested as diseases. For example, hemophiliae A and B are due to a decrease of blood coagulation factors VIII and IX respectively and are typified by bleedings especially in the joints and in the musculature.

In the past years, it became evident that the prognosis of hemophilia-affected persons can considerably be improved by substitution therapy using preparations containing factors VIII or IX.

So far, the starting material known for the manufacture of medicaments substituting factors VIII or IX has only been blood plasma or fractions thereof. It has also been known for a longer time, that the aqueous extract of placentae is a strongly coagulation-active material whose activity is to be typified as thromboplastic material. Such preparations are physiologically incompatible. They cannot be used in therapeutic treatment.

The extraction of placentae by means of lipid solution methods also leads to a coagulation-active partial thromboplastin. However, the coagulation-active material so obtained does not have the properties required for antihemophilia A and B substitution therapy.

It was surprisingly found that a thromboplastic material obtained by the aqueous extractions of placentae can be brought into a form suitable for substitution therapy. The antihemophilic agent so obtained can be isolated and, if desired, further purified.

An object of the invention is an antihemophilic agent characterized by its property to substitute the coagulation factors VIII, IX, VII and X in deficient plasmae. It can also be characterized by the activity proportion of the factors VIII, IX, VII and X.

The antihemophilic agent can be obtained by a method according to which comminuted placentae washed until free of blood are extracted with an aqueous hypotonic medium at a pH value in the weakly acid, neutral or alkaline range, the extract is separated from the residual tissue, the specific density of the extract is increased by adding an inert water-soluble compound until coagulation-active compounds having the above-cited coagulation activities have creamed up, the supernatant layer forming is separated and, if desired, further purified.

For further purification, the flotation can be repeated.

Inert, water-soluble compounds in this invention are all physiologically tolerable substances which do not react with the constituents of the extracts. Especially suitable are physiologically tolerable salts or water-soluble carbohydrates.

Futher purification can be effected by the extraction of the supernatant layer, diluted with an aqueous medium, at low conductivity and a weakly acid pH value using a solvent for lipids which is immiscible with water, preferably a hydrocarbon or an alkyl ether, having a boiling point within the range of from 40 to 80° C, in the presence of a coagulation-inert protective colloid and a polar, polyionic compound capable of forming a complex with polypeptides or proteins, preferably a polyanion such as a polysaccharide-polysulfuric acid compound, for example heparin, or a polycation, for example protamine. In this process, the antihemophilic agent is enriched in the aqueous phase and can be obtained therefrom. Purification can also be effected by ultracentrifugation of the redissolved supernatant layer in the presence of a coagulation-inert protein.

Purification can also be effected by treating the supernatant layer with aqueous sodium hydroxide solution and separating the dialysable substances.

Finally, further purification can be effected by dissolving the supernatant layer in an aqueous sodium chloride solution as described below and by chromatographing this coagulation-active sodium chloride solution in the presence of a coagulation-inert lipophilic protein through a molecular sieve, whereafter the factor VIII, IX, VII and X containing fractions of the eluate are obtained.

The antihemophilic placenta substance can also be purified in ways already described for the elimination of known factors influencing coagulation. Thus, the portions of prothrombin which are capable of decreasing the factor-VIII-activity of the product of the invention can be eliminated by absorption on aluminum hydroxide or barium sulfate, by precipitation with acridine bases, or by chromatography on ion exchanger resins.

The antihemophilic agent obtained according to this process can be used, for example, as a diagnostic agent in all coagulation tests which are to show a factor VIII, IX, VIII and X activity.

In the present invention, comminuted placentae washed until free of blood are used. Human placentae are preferred. Fresh or lyophilised placentae for storage can be comminuted and repeatedly washed with an isotonic salt solution to eliminate the blood and plasma constituents. The washed placental homogenate is obtained by filtration or centrifugation and subsequently dried, if desired. Lyophilisation is preferred as a specially mild drying method. The dry placental tissue washed until free of blood is preferably extracted in a 4 – 10%, especially 5 – 7%, suspension using an aqueous hypotonic medium at a pH ranging between 4.5 and 14. Water or hypotonic salt or buffer solutions are preferred, their concentration and electrolyte composition leading to an osmotic concentration of $\leq 330$ mM/1.

Especially suitable are neutral salt solutions, their pH being adjusted to the desired value, after the suspension of the placental tissue in solution, with bases, such as sodium hydroxide solution or sodium carbonate solution. The extraction of the placental tissue with the hypotonic solution can be performed at any pH value ranging between 4.5 and 14.

In a special embodiment of the invention, comminuted placentae washed until free of blood are extracted at $pH > 4.5$ with an aqueous medium having an osmolarity of $\leq 330$ mM/1, the extract is separated from the residual tissue and subjected to a flotation. To increase the density of the solution, an inert water-soluble compound, for example a neutral salt or a carbohydrate, preferably an alkali metal or alkaline earth metal halide such as KBr, NaBr, or $CaCl_2$, or saccharose, is added to the aqueous extract. The added amount of suitable substances gives a density of the solution of at least 1, the upper limit being given by the solubility of the salts, preferably a density of 1.06 to 1.20 g/cm³. Then, the solution is centrifuged for at least 60 minutes, preferably 120 minutes, by speeding up to $\leq 25,000 \times$ g, preferably 50,000 × g. After centrifugation, the somewhat dull layer floating atop the lower clear salt solution is separated. The flotation of the dull layer in the centrifuge is repeated advantageously under identical or comparable conditions, for example at a speed of 50,000 - 150,000 × g and the supernatant layer is finally obtained.

Suitable flotation systems for the separation of lipoproteins from blood plasma are known to those skilled in the art. When a 20% aqueous potassium bromide solution is used and the ultracentrifuge turns at a speed corresponding to 50,000 × g, the antihemophilic-active fraction floats at the surface of the solution after about 2 hours. It is largely free of residual protein constituents which are settled or remain in solution. The supernatant layer so obtained is dispersed in water or a diluted salt solution, for example a 0.5 to 1.2% sodium chloride solution, preferably a 0.9% sodium chloride solution, and the factor VIII and IX-activities are determined on a sample taken therefrom.

The dispersion is diluted such that the dilute solution of the layer material contains from 10 - 200, perferably 20, factor VIII units.

The crude preparation of the antihemophilic agent obtained by flotation can be subjected, if desired, to one or several of the following purification processes. At least one of these purification processes is necessary if the product is to be used for intravenous therapy.

1. Purification by extraction

To the product obtained by flotation over a concentrated salt solution and having a factor-VIII-activity of 10 - 200, preferably 20 units, are added a coagulation-inert protein, for example albumin, preferably human albumin, in a concentration of 1 - 10%, preferably 5%, and then a polyanion capable of forming a complex with basic polypeptides, proteins and/or phospholipids, preferentially a polysaccharide-polysulfuric acid compound such as heparin, preferably its sodium salt, in an amount of from 0.005 to 0.5 mg/ml, in the case of heparin correspondingly from 1 - 50 units per ml of the solution. Thereafter, a conductivity of <14 mS/cm is adjusted by diluting or by adding salt — the latter being generally necessary — and the pH is adjusted to 3.5 - 6 with acid, preferably a mineral acid such as hydrochloric acid. One part by volume of the suspension obtained is shaken at least once for 2 - 8 hours at 10° - 40° C, preferably at room temperature, with at least 1 part of a solution for lipids which is immiscible with water and which has a boiling point of 40° to 80° C, preferably with an aliphatic ether or a hydrocarbon having a boiling point within the given range, or a mixture thereof, any mixing ratio being possible, a mixture of 8 parts by volume of petroleum ether and 2 parts by volume of diethyl ether being preferred. A mechanical shaking or mixing apparatus is advantageously used. After being allowed to stand for a short time, the organic phase can be separated or rejected. The aqueous phase is freed from residual solvents, advantageously in vacuo. Then, the factor VIII and IX-activity is determined in known manner. The product can be used for parenteral administration.

Instead of a polysaccharide-polysulfuric acid compound, a polycationic compound can also be used in the invention, such as protamine, preferably its chloride or sulfate, in a concentration of from 1 - 10 mg/ml, to obtain a product having a comparable factor VIII-activity.

For parenteral administration, 10 to 500 units of factor VIII, preferably 20, are advantageous as a single dosage unit in solution. A prior filtration under sterile conditions for the elimination of contaminating microorganisms is necessary. Then, the preparation can be brought into a form suitable for parenteral administration to which stabilizing protective colloids, for example protein, are added and can subsequently be lyophilised, if desired. The physiologically tolerable solution of the product of the invention or the redissolved lyophilised preparation can be used for substitution therapy, for example the treatment of hemophilia A.

Suitable solvents are, for example distilled water and physiological NaCl-solution, if desired with the addition of a buffer substance such as a 0.02 molar Na-citrate having a pH value of 7.

Before lyophilisation, protective colloids such as albumin and/or carbohydrates such as fructose may be added to the preparation for its stabilisation. With regard to therapeutical use of the final products in human beings, human albumin is advantageously used.

Futher purification processes are mentioned below. However, the process described under No. 2 is less suitable for the manufacture of a pharmaceutical composition.

2. Purification by treatment with alkalis

A solution containing 10 - 200 factor VIII units is adjusted to pH 10 to 14, preferably 12, with sodium hydroxide solution, for example 2 - 7 N, preferably 5 N,NaOH. The batch is allowed to stand at this pH for 15 minutes to 48 hours, then it is neutralised, i.e. the pH is adjusted so as to approach the neutral point, preferably between 6 to 8, using inorganic acids, for example 2 - 10 N, preferably 5 N,HCl. Low-molecular weight constituents are separated by dialysing the neutralised solution against a physiological salt solution, for example an isotonic sodium chloride solution. Before, during, or after the dialysis, coagulation-inert additives may be added to stabilise the activity of the antihemophilic agent. Inert protein material, for example albumin, is especially advantageous.

3. Purification by chromatography

An aqueous solution containing 10 - 200 factor VIII units can also be purified by fractionation on a molecular sieve, for example by gel filtration in a column. As the molecular sieve, an agarose specially worked up is expedient, for example the one available from Pharmacia, Uppsala, Sweden under the trade mark Sepharose (R) or from Bioral Laboratories, Richmond-/Calif. under the trade mark Biogel A(R). The fractionation range of this material should be for globular molecules having molecular weights from $10^4$ to $10^6$. Before carrying out the molecular sieve chromatography, the antihemophilic agent is advantageously dialysed against a dilute, preferably an about isotonic, salt solution and then is advantageously adapted as extensively as possible, from the viewpoint of the quality and quantity of further additives thereto, to the solution is used for the elution of the desired product in the molecular sieve chromatography. The elution solution contains neutral salts, for example sodium chloride, in a concentration of from 0.7% to 5.8%, preferably 4.5 to 5%, and a stabilising additive in the form of an inert protein, for example albumin, in a concentration of from 1 - 10%, preferably 3%. The chromatography is performed in known manner.

The fractions obtained are selected with respect to content of factor VIII—, VII— and IX-activity, the fractions having an enriched factor VIII-activity being collected and combined and optionally adjusted to the desired factor VIII units using a physiological salt solution, or, if necessary, concentrated by means of an ultrafilter to reach the desired number of factor VIII units.

The aforementioned purification process is suitable for additional purification of the products obtained according to the methods described, and especially for replacing dialysis in the process employing treatment with alkalis.

4. Purification by centrifugation

The crude product obtained by flotation over concentrated salt solutions is diluted with distilled water to 10 - 200 factor VIII units, preferably 100 units to which sodium chloride is added to reach a concentration of 0.075 to 1.0 M, preferably 0.15 M. Then, a coagulation-inert lipophilic protein, for example albumin, preferably human albumin, is added to the solution up to a concentration of 1 - 10%, preferably 2.5 to 5%. The mixture is incubated at 37° C for 1 - 10 hours, preferably 2 - 5 hours. Then, the mixture is centrifuged at a speed of 50,000 × g for 30 - 120 minutes, preferably for about 60 minutes, and the supernatant solution containing the antihemophilic agent is obtained.

After addition of usual protective colloids and corresponding stabilisers, the nearly clear centrifuged mixture is filtered under sterile conditions.

The yield of factor VIII and IX-activity is examined advantageously during the working-up process and/or thereafter. It is determined for example according to the following method:

1 part, for example 0.1 ml, of partial thromboplastin (for example that prepared according to German Patent Application P 23 16 430) is mixed with one part of factor VIII-deficiency plasma and one part of dilute normal plasma. The temperature of this mixture is kept at 37° C for 6 minutes. After the addition of one part of a 0.025 molar calcium chloride solution preheated to 37° C, the time expiring between the addition of the calcium chloride solution and the formation of a solid coagulate is measured. To make a quantitative evaluation, the coagulation time resulting from a factor VIII-containing solution is read off in relationship to a calibration curve obtained with the aid of a normal plasma dilution series.

1 unit of factor VIII corresponds to the factor VIII-activity of 1 ml of normal plasma.

The determination of the factor IX-activity can be effected according to the method described for the determination of the factor VIII using instead of the factor VIII-deficiency plasma a factor IX-deficiency plasma.

The factors VII and X are determined in an analogous manner using congenital factor VII and X-deficiency plasma, respectively.

A further object of the invention is an antihemophilic agent having factor VIII, IX, VII and X-activity obtainable according to one of the above-cited processes.

A further object of the invention is a medicament suitable for the intravenous substitution therapy of hemophilia A and B consisting of or containing an antihemophilic agent obtainable according to one of the above-cited processes and optionally containing pharmaceutically usual carriers as additives. For stability reasons, the preparation is stored advantageously in dry lyophilised form. Before being administered intravenously, the dry product is to be reconstituted in the manner known for such preparations.

The preparation substitutes:

1. Factor VIII and IX deficiencies, tested according to the partial thromboplastin time method (PTT) on the corresponding congenital deficiency plasmas. The activity can be indicated in units with reference to standard human plasma (1 u/ml). The factor IX-activity was determined for several charges with 0.5 - 1 units per unit of factor VIII;
2. Factor VIII of inhibitor hemophilia occurring in polytransfused patients suffering from hemophilia A;
3. Congenital factor X-deficiencies determined according to the PTT method and the Russel-Viper-Venom time method.

Thus, the hemostyptic from placentae substitutes all the factors of the endogenic activation mechanism to a greater or smaller extent, the substitution of factor VIII being most efficient; furthermore:

4. Congenital factor VII-deficiencies are normalised, measured according to the PTT method and the single phase coagulation time method according to Quick;
5. Cumarin-induced coagulation deficiencies which lead to the formation of prothrombin incapable of being physiologically activated (prothrombin induced by Vitamin K Absence = PIVKA) are partially substituted. The correction is very likely in the order of magnitude of the prothrombin which can still be activated: 15 - 20% of the activity of normal plasma in well stabilised patients;
6. Prothrombin (highly purified, free of factor VII and X) is activated, too, but only moderately.

After the addition of decalcified human plasma, the active principle is stable for several hours; an inhibition occurs only after the addition of herparin, which acts as an antidote.

Of the factors of the endogenic coagulation system, factor VIII and IX are substituted by the hemostyptic of placentae with special efficiency, and factor VII and X only partially. As to its composition and properties, the hemostyptic of placentae is a complex which contains a relatively small protein portion, but a high phospholipid portion, the properties of a real solution being conferred to it by the addition of albumin.

The hemostyptic of human placentae contains the phospholipid necessary for the formation of the factor X-activator in an especially efficient form. The wide therapeutic effect is additionally sustained by a substance that is similar to or even identical with the activated factor X. It directly catalyses the conversion of prothrombin into thrombin without the need of factors VIII and IX, its effect being unaffected by inhibition bodies. The hemostyptic of human placenta is a preparation that enables a new therapy of hemophilia. This comprises not only the large field of application, but also the crude product. The manufacturing process, the composition, and the mode of action of the hemostyptic differ from those of other preparations known in the art. The main indication is probably the treatment of inhibition body hemophiliae which could be treated heretofore only using animal antihemophilic globulin as the coagulation factor, or with activated factors.

The following Example illustrates the invention in detail:

EXAMPLE

Lyophilised placental tissue washed until free of blood is intimately homogenized in a 5% suspension in 0.05 M Na-citrate solution for 20 minutes at room temperature. The homogenizate is centrifuged for 30 minutes at 30,000 × g, the sediment is rejected and the supernatant formed is brought to 20% of saturation with solid potassium bromide. The extract is centrifuged for 2 hours at 50,000 × g in an ultracentrifuge, giving a fluid readily to be separated. This supernatant zone is taken off. Since physiological compatibility of the preparation is required, it is advantageous for intravenous substitution therapy only to use preparations which are subjected to one of the foregoing purification processes. After a new flotation at 150,000 × g, the preparation is ready for use as a factor VIII agent. The activity of the factors VIII, IX, X and VII is tested.

The factor VIII-activity is 200 U/ml.

Continuation of purification:

a. The preparation floated in 150,000 × g of diluted at equal parts with an aqueous 10% human albumin solution which contains 10 U/ml of heparin-sodium.

It must be taken into account that the total salt content of the mixture corresponds to an electrical conductivity of about 8 mS/cm. The pH is adjusted to 4.5 with 1 N HCl.

The mixture is put into an extraction apparatus according to Kutscher and Steudel and continuously extracted for 2 hours with 2 parts of a mixture of petroleum ether (b.p. 60°–80° C) and diethyl ether = 80/20 (vol/vol).

After that operation, the organic solvent is eliminated under mild conditions in vacuo at 20° C by means of a rotation evaporator and the remaining aqueous phase is adjusted to pH 7.5 – 8 with 1 N NaOH. After stirring for 2 hours at room temperature and filtration under sterile conditions, the preparation is ready for use in the substitution therapy of factor VIII deficiencies. The factor VIII-activity of a sample is adjusted to about 30 U/ml.

Instead of heparin-sodium, protamine sulfate (5 mg/ml) may be added to the factor VIII preparation in the first process step.

b. The preparation floated at 150,000 × g is diluted with a 0.15 M NaCl-solution having a 5% content of human albumin to an activity of about 100 units of factor VIII. After an incubation period of 5 hours at 37° C, this mixture is centrifuged for half an hour at 50,000 × g and after the addition of 1% of fructose the nearly clear centrifuged liquid is filtered under sterile conditions.

In animal tests, for example on rabbits, this preparation proves to be toxicologically compatible. Its effect on healthy animals is comparable to that of a concentrate of antihemophilic globulin from plasma.

The following Table is a summary of the effect of the hemostyptic from human placentas on plasma coagulation periods of normal plasma, factor-deficiency plasmas and plasmas with inhibitor of factor VIII determined according to the PTT*).

| Plasma | Control | Hemostyptic Solution ready for use | |
|---|---|---|---|
| | | dilution 1:20 0.1 U**/mixture | dilution 1:10 0.2 U/mixture |
| normal Plasma | 45.6"*/45.2" | 31.9"*/32.6" | 28.8"***/28.8" |
| factor VII-deficiency plasma | 56.6"  /56.8" | 43.5"  /43.9" | 37.3"  /37.5" |
| factor VIII-deficiency plasma | 137.6"  /137.9" | 42.2"  /42.4" | 33.7"  /33.6" |
| inhibition-body-hemo-philia plasma | 128.6"  /128.2" | 39.4"  /39.8" | 31.7"  /31.7" |
| factor IX-deficiency plasma | 136.6"  /136.4" | 44.3"  /44.2" | 34.8"  /34.5" |
| factor X-deficiency plasma | 126.0"  /126.5" | 73.7"  /73.9" | 64.0"  /63.7" |

*test mixture for PTT: 0.1 ml of normal or deficiency plasma (DPL)
0.1 ml of placenta-factor VIII (0.1 U or 0.2 U) or buffer, pH 7
0.1 ml of pathromtin(R)
120 ml to incubate
0.1 ml of CaCl$_2$
**calculated on factor VIII-activity of normal plasma: 1 U/ml
***" = sec.

What is claimed is:

1. A method for making an antihemophilic agent, which method comprises comminuting placental tissue, washing the comminuted tissue with an aqueous hypotonic medium at a slightly acid to alkaline pH until the tissue is free of blood, extracting the washed tissue at a pH above 4.5 with an aqueous solution having an osmolarity below 330 nanomoles per liter, removing residual tissue from the extract, adding an inert water-soluble compound to the extract, whereby its density is increased, until separation and the flotation of a supernatant layer occur, and then isolating the supernatant layer, which contains said antihemophilic agent.

2. A method as in claim 1 wherein said isolated supernatant layer is subjected to further purification.

3. A method as in claim 2 wherein said supernatant liquid is further purified by repeating the flotation.

4. A method as in claim 2 wherein said supernatant layer is further purified by diluting it with an aqueous medium and then extracting it, at low electrical conductivity and a slightly acid pH, with a water-immiscible solvent for lipids, in the presence of a coagulation-inert protective colloid and of a polar polyionic compound capable of forming a complex with polypeptides or proteins, whereupon the antihemophilic agent is enriched in the aqueous phase with respect to factor VIII—, IX—, VII—, and X— activity.

5. A method as in claim 2 wherein said supernatant layer is further purified by combining it with aqueous sodium hydroxide solution, neutralizing the mixture to a pH between 6 and 8, and dialyzing it to remove low molecular weight constituents.

6. A method as in claim 2 wherein said supernatant layer containing factors VII, VIII, IX, and X, is further purified by dispersing it in an aqueous salt solution, chromatographing the mixture on a molecular sieve using an eluent containing a coagulation-inert protein, and collecting those fractions containing factor VIII.

7. A method as in claim 2 wherein said supernatant layer is further purified by dispersing it in an aqueous salt solution, adding a coagulation-inert protein to the mixture, centrifuging the mixture to separate a new supernatant layer, and isolating said new supernatant layer, which is enriched in factor VIII.

8. An antihemophilic agent prepared by the method of claim 1.

9. An antihemophilic agent prepared by the method of claim 2.

10. An antihemophilic agent prepared by the method of claim 3.

11. An antihemophilic agent prepared by the method of claim 4.

12. An antihemophilic agent prepared by the method of claim 5.

13. An antihemophilic agent prepared by the method of claim 6.

14. An antihemophilic agent prepared by the method of claim 7.

15. A pharmaceutical composition for the treatment of hemophilia which comprises an antihemophilic agent as in claim 9 in combination with an intravenously administrable pharmaceutical carrier.

16. The method of treating hemophilia by substitution therapy which comprises intravenously administering to a patient suffering from hemophilia an amount of an antihemophilic agent as in claim 9 sufficient to correct coagulation factor deficiencies.

* * * * *